United States Patent [19]

Tantram et al.

[11] 4,324,632

[45] Apr. 13, 1982

[54] GAS SENSOR

[75] Inventors: Anthony D. S. Tantram, Great Bookham; Yat S. Chan, London, both of England

[73] Assignee: City Technology Limited, London, England

[21] Appl. No.: 150,025

[22] Filed: May 15, 1980

[30] Foreign Application Priority Data

May 17, 1979 [GB] United Kingdom ............... 17237/79

[51] Int. Cl.$^3$ ............................................ G01N 27/30
[52] U.S. Cl. ................................................ 204/195 P
[58] Field of Search ........................... 204/195 P, 1 P; 128/635

[56] References Cited

U.S. PATENT DOCUMENTS

| | | | |
|---|---|---|---|
| 3,787,308 | 1/1974 | Malaspina et al. | 204/195 P |
| 3,795,589 | 3/1974 | Dahms | 204/1 T |
| 4,092,232 | 5/1978 | Zetter | 204/195 P |
| 4,132,616 | 1/1979 | Tantram et al. | 204/195 P |
| 4,166,775 | 9/1979 | Bruckenstein et al. | 204/1 T |
| 4,169,779 | 10/1979 | Tataria et al. | 204/195 P |
| 4,207,161 | 6/1980 | Pegnim | 204/195 P |

OTHER PUBLICATIONS

Luikov, A. V., "Heat and Mass Transfer in Capillary-Porous Bodies", pp. 220-225, (1966).
SMRE Digest, Gas Detection, 1, 1975.

Primary Examiner—G. L. Kaplan
Attorney, Agent, or Firm—Sughrue, Mion, Zinn, Mackpeak & Seas

[57] ABSTRACT

An electro-chemical sensor for the measurement of concentrations of gas or vapour in accordance with the limiting current principle comprises an electrolytic cell 1 having a sensing electrode 9, a counter electrode 2, an intervening body of electrolyte 4 and a restriction to the rate of access of gas or vapor to the sensing electrode in the form of a porous diffusion barrier 13. The improvement resides in the feature that substantially all the active pores of the diffusion barrier are sufficiently small as to cause diffusion through them to be in accordance with the Knudsen principle, i.e. the diffusion mechanism is effectively determined solely by collisons between the diffusion molecules and the walls of the pores. The barrier is constituted by a body of porous PTFE which may be in the form of a piece of unsintered PTFE tape or compressed PTFE powder formed by drying a dispersion of PTFE in water.

9 Claims, 6 Drawing Figures

GAS SENSOR

This invention relates to electro-chemical gas sensors in which the gas or vapour to be sensed is caused to react at one electrode of an electro-chemical cell, which also includes a counter electrode and an intervening body of electrolyte, in such a way that the current through the cell is a function of the partial pressure of the gas or vapour to be sensed. The principle will be described in relation to the sensing of oxygen although it is to be understood that it is applicable to any gas or vapour which can be electro-chemically reacted in this way. Gases or vapours such as, for example, oxygen and nitrogen oxides which are electro-chemically reducible, are sensed at the cathode, while those which are electro-chemically oxidisible, such as carbon monoxide, sulphur dioxide and hydrogen sulphide are sensed at the anode.

In practice oxygen is electro-chemically reduced at an oxygen cathode, to which the rate of access of oxygen is restricted, for example by a diffusion barrier, under conditions such that the electrode is operating in the so-called limiting current region. The general principles and practical considerations involved are described in some detail in U.S. Pat. No. 4,132,616. In particular, FIG. 1 of the drawings of this earlier specification illustrates the limiting current principle.

There is a continuing demand for reliable and easy to operate gas sensors. Oxygen sensors, for example, are required for oxygen deficiency monitoring for safety purposes where personnel have to work in confined spaces. Here small, portable, inexpensive, robust and reliable sensors, which can readily be used by unskilled personnel and which are substantially unaffected by ambient changes, e.g. temperature, humidity, are most important. Oxygen measurement is also important in a wide range of other applications, e.g. combustion control, process control and other industrial applications. In some applications it is the partial pressure of oxygen that is the important parameter, for example for measurement of breathing gases at pressures appreciably differing from ambient. In others the concentration, or percentage oxygen is the more important parameter, for example in process control applications. In cases where no pressure changes are encountered, it is not greatly significant whether the sensor measures partial pressure or percentage.

As explained in the U.S. specification, most of the known types of gas sensors working on these general principles achieve the necessary restriction to the access of gas to the sensing electrode by the provision of a non-porous solid membrane between the body of the gas to be tested and the sensing electrode so that the flux of gas is restricted by the diffusion rate of gas in solution in the solid membrane. Examples of such solid membranes that have been used are films of polytetrafluoroethylene, polyethylene and silicone rubber. An example of a sensor using such a membrane is that described in S.M.R.E. Digest, Gas Detection, 1. 1972.

The use of non-porous solid membrane films has the disadvantage that very thin membranes have to be used to achieve practical current levels and more importantly that the resulting sensor has an extremely high temperature co-efficient, which may be as high as 2% to 3% per degree centigrade. This means that provision must be made for temperature compensation and this is difficult to achieve accurately and reliably. This high temperature co-efficient is a fundamental consequence of the process of transporting gas in solution through a solid material, being associated with the high activation energy required for this purpose.

The U.S. specification referred to above describes and claims a form of gas sensor which includes a gas phase diffusion barrier (referred to subsequently as a GP barrier) to provide the necessary controlled restriction to the access of gas to the sensing electrode. This barrier may be in the form of a simple capillary, a porous sheet or a combination of these.

The essential features of a GP diffusion barrier are:

(a) that the gas remains in the gas phase during its diffusion through the barrier (b) that the diffusion resistance is provided by the molecules of the gases present (hence the term gas phase diffusion barrier) so that the diffusion mechanism and hence the laws governing diffusion are determined by inter-molecular collisions in the gas phase. The capillary or porous sheet serves to contain this gas phase diffusion barrier and control and define its geometry.

It will be seen from the description above that the characteristics of the resulting sensor depend upon the type of diffusion barrier used.

According to the present invention, a sensor operating on the limiting current principle as described above, utilises a porous diffusion barrier to provide the necessary limitation to the rate of diffusion of gas to be sensed, of which substantially all the active pores are sufficiently small as to cause diffusion through them to be in accordance with the Knudsen principle. Diffusion in accordance with this principle is characterised by the fact that the diffusion mechanism is effectively determined solely by collisions between the diffusing molecules and the walls of the pores and the term "Knudsen diffusion" is used in this sense throughout the specification and claims, references to a Knudsen diffusion barrier being abbreviated to KD barrier for convenience.

Details of Knudsen diffusion have been described, for example, in "Heat and Mass Transfer in Capillary-Porous Bodies", Luikov. A. V., Pergamon, 1966. The mechanism of this type of diffusion is radically different from that applying to the diffusion barriers already described namely, the GP barrier, controlled by inter-molecular collisions in the gas phase and the solid membrane barrier (SM barrier) controlled by diffusion in solution. Consequently the laws governing diffusion are different and this in turn leads to sensors having significantly different characteristics from GP barrier or SM barrier sensors, and to characteristics which give rise to specific advantages in specific situations.

Thus, for example, KD barrier sensors have an intrinsically low negative temperature co-efficient of about $-0.17°$ C. per °C. in the ambient range (reflecting a $T^{-\frac{1}{2}}$ law resulting from the Knudsen diffusion mechanism, where T is the absolute temperature), which is sufficiently low for temperature compensation not to be necessary in many applications. This temperature co-efficient is in marked contrast to the high positive co-efficient of SM barrier sensors and also differs from GP barrier sensors in that it is negative rather than positive. It is also found that sensors according to the present invention respond to partial pressure rather than concentration (% by volume) and that the response to partial pressure is linear over a wide range, thus distinguishing them further from GP barrier sensors.

In the selection of suitable materials for KD barriers, pore size is the primary criterion. As explained above, the phenomenon of Knudsen diffusion is determined by collisions between the gas molecules and the walls of the pores and thus imposes the requirement that the size of the pores in the KD barrier are sufficiently small that the number of inter-molecular collisons becomes insignificant compared to the number of molecule to wall collisions. As a starting guide it can be said that the pore diameter needs to be less than the mean free path of the gas molecule in question. In the case of oxygen for example, this is about $9.5 \times 10^{-6}$ cm at ambient temperature and pressure. As mentioned previously, it is necessary that substantially all the pores throughout the barrier should be well into the "Knudsen" region to ensure that Knudsen diffusion is the governing mechanism.

Such small pore sizes, and their distribution, are difficult to measure and as a result selection of materials by attempts at direct measurement of pore size is unsatisfactory. Moreover, we have found that manufacturer's specifications as to pore size cannot be taken as a reliable guide in this context. For these reasons, and since it is the diffusion characteristics that are the property most directly pertinent to this invention, materials are best selected by a direct examination of the diffusion characteristics.

As described above, a specific characteristic is the low negative temperature co-efficient and it can therefore be deduced that, if the diffusion rate has a negative temperature co-efficient of around $-0.17\%$ per °C. at ambient temperatures, the material under test should be a satisfactory KD barrier. This theoretical temperature co-efficient of $-0.17\%$ per °C. may be modified slightly in practice due to differential thermal expansion effects. A convenient way of carrying out such a test is in fact to make up an oxygen sensor incorporating the diffusion barrier and to measure its temperature co-efficient. To carry out such tests the diffusion barrier needs to be suitably mounted and effectively sealed in position. Since it is necessary that Knudsen diffusion should be the controlling gas transport mechanism it is clear that any leakage path, along which Knudsen diffusion would not occur, needs to be avoided. Measurement of the pressure co-efficient will provide a confirmatory test, since the diffusion rate (or signal from the oxygen sensor at a given % oxygen) will be substantially proportional to total pressure for a KD barrier, whereas for a GP barrier, such as described in the U.S. specification, the diffusion rate (or signal from the oxygen sensor at a given % oxygen) is substantially independent of total pressure.

Tests, such as those described above, with a wide range of materials have brought to light a further desirable criterion to ensure that a satisfactory KD barrier is achieved in practice, namely the aspect ratio of the barrier. More specifically if a simple case is considered where the KD barrier is in the form of a cylinder with diffusion occurring along the length of the plug, then the diameter of the barrier plug should be less than twice the length of the plug. It will be appreciated, as will be illustrated later, that the KD barrier can take a variety of different geometric shapes. The criterion illustrated above can be therefore stated in a more general form as follows:

The ratio $x/L$ should be less than 2 where $x$ is the minimum linear dimension across the part of the KD barrier through which diffusion is occurring in the direction at right angles to the overall direction of diffusion and $L$ is the mean linear dimension along the overall direction of diffusion. Should the KD barrier effectively comprise a number of individual KD barriers in parallel then the dimension $x$ refers to the individual KD barrier.

It is found that various commercially available porous PTFE tapes, often referred to as "unsintered" tapes, may have sufficiently small pores as to give Knudsen diffusion, but the properties of such tapes are somewhat erratic and are found to vary from one production batch to another. Accordingly it is necessary to subject any sample of such tape to the previously described test for diffusion. If the result of such a test is unsatisfactory it may be possible to improve the diffusion characteristics. Such tapes are anisotropic and, in one direction, usually along the length of the tape, are resistant to stretching. In the other direction, i.e. across the width of the tape, they can be readily stretched to several times the original widths. It has been found in a number of cases that this treatment will produce a material giving Knudsen diffusion, and suitable for a KD barrier, particularly when mounted so that diffusion through the barrier was along the direction of stretching, even when the starting tape was unsuitable, as evidenced by the tests mentioned earlier. If the results are still unsatisfactory, the sample must be rejected.

The following are some examples of commercially available tapes that have been found to have the required characteristics:

(1) A 0.24 mm thick PTFE tape supplied by W. L. Gore and Associates (UK) Limited, described as clear, unsintered, unstretched tape and having a porosity of about 15%;

(2) "Gore-tex" S10633 from the same suppliers;

(3) "Tygaflor" R 128 gauge 7T supplied by Tygadure Limited.

In a particular example a tape in accordance with (1) above was stretched laterally to six times its original dimension. The effect of stretching was found slightly to increase the thickness to 0.32 mm, but radically to reduce the longitudinal dimension as the lateral dimension was increased. Using a piece of the resultant membrane having a length in the stretched direction of 3 mm and a width of 1.5 mm as a diffusion barrier in an oxygen sensor, mounted, as described later, and in such a way that the diffusion through the tape was along the direction of stretching, gave a resultant temperature co-efficient of $-0.175\%$ per °C. when measured over the range 10° C. to 40° C.

Other commercially available material from which a membrane yielding Knudsen diffusion may be obtained is a dispersion of PTFE in water such as that manufactured by Imperial Chemical Industries Limited under the name "GP1" and a similar dispersion manufactured by Du Pont de Nemours Inc. The dispersion comprises minute particles of PTFE in suspension and when dried and the dispersing agent removed, yields a pasty mass which may be readily consolidated by the application of pressure. The dispersing agent may be removed, for example by solvent extraction or by heat treatment at around 270° C. for about one hour.

The pressure required for consolidation is to some extent dependent on the geometry of the KD barrier being constructed, but may be readily established by experiment. As a guide it has been found that so long as the pressure is above about 1000 psi the resultant compact will normally yield Knudsen diffusion and be suitable for a KD barrier, as indicated by the diffusion/sensor tests already mentioned.

By consolidating the material in situ in a suitably sized hole in the sensor top cap, it is caused to conform with the shape of the hole and thus to prevent any leakage. In a particular example, a quantity of the pasty material referred to was pressed into a hole of diameter 1.5 mm and length 1.3 mm and was consolidated at a pressure of about 2000 psi. This gave an oxygen sensor having a temperature co-efficient of 0.165% per °C., thus demonstrating that the resultant pores were small enough to produce Knudsen diffusion.

Other constructional features will now be described in more detail with reference to the accompanying drawings, (not to scale), in which.

Figure 1:
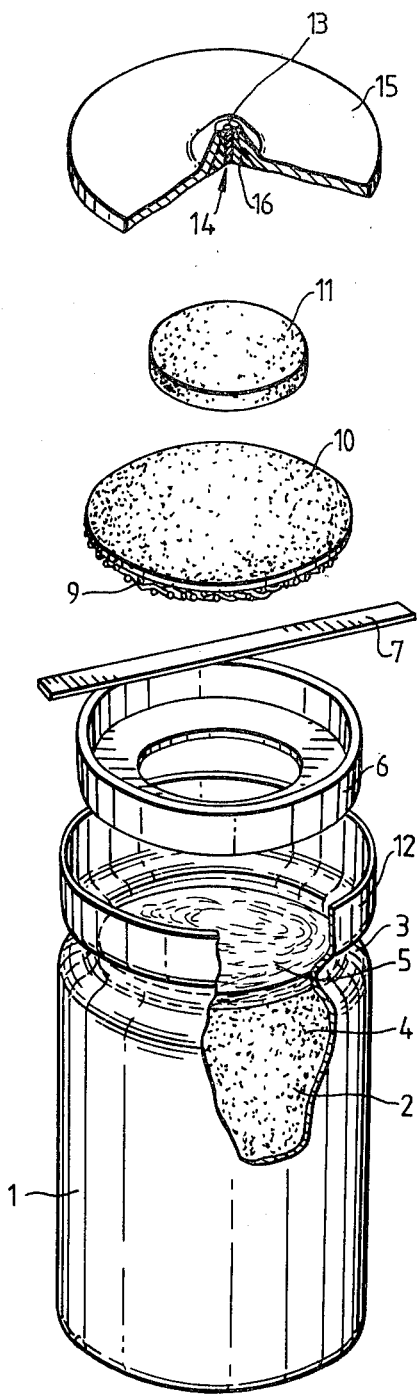
FIG. 1 is an exploded perspective view of a complete sensor including a top cap fitted with a KD barrier.

The basic construction of cell shown in FIG. 1 is similar to that illustrated in the U.S. patent referred to previously and comprises a metal can 1, for example of nickel plated steel, which contains and electrically contacts a counter-electrode 2 which forms the anode when the device forms an oxygen sensor. The electrode 2 may, for example, be of lead wool extending up to just below the level of a rill 3. The porous electrode 2 is filled with electrolyte 4, for example sodium hydroxide. A wicking separator 5 which is permeable to electrolyte but is electrically insulating is fitted on top of the electrode 2 and above this is an insulating grommet seal 6. A narrow strip of thin metal foil 7, for example silver, connects a sensing electrode 9 to the outside of a metal top cap 15 when the cell is finally closed. A waterproofing layer 10 of porous PTFE is pressed to the electrode 9 to form a unitary assembly and a porous disc 11, for example of plastic, is fitted immediately beneath the top cap 15 to ensure a good spread of diffusion of gas passing through the top cap 15. The components just described are stacked one on top of the other and the assembly is completed by folding over an upper rim 12 of the can 1 to hold all the components in position.

The top cap 15 shown in FIG. 1 constitutes one example of which the remaining Figures show further examples. The top cap 15 has a central opening 14 surrounded by a raised portion of the cap and a KD barrier 13 is fitted in this opening, being sealed in position by melting of a hot melt adhesive or by potting with a resin shown as 16. In this example, the KD barrier 13 is constituted by a piece of stretched PTFE tape as previously described which is mounted so that the diffusion path through the barrier is along the direction of the stretch. In assembly, a longer than necessary length of tape is used so that it can subsequently be trimmed flush at the top and bottom of the top cap 15.

Figure 2:
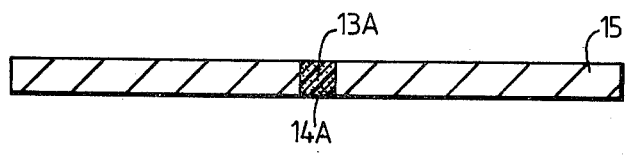
FIGS. 2 and 3 are cross sectional views to an enlarged scale of alternative constructions of top cap for substitution in the construction of FIG. 1.
Figure 3:
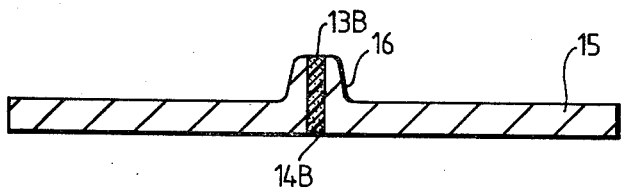

FIGS. 2 and 3 show top caps 15 designed for KD barriers formed of pressed PTFE powder, as previously described. In FIG. 2 a central opening 14A is formed within the thickness of the cap 15 and in FIG. 3, a central opening 14B is formed within a thickened portion 16 of the top cap to give a greater length of barrier. The barrier itself is shown as 13A and 13B respectively in the two Figures and in each case, during manufacture, the PTFE powder is extruded into the openings 14A, 14B and then consolidated by pressure, preferably in a mould incorporating elastic rubber discs against the top and bottom of the top cap 15, in order to improve sealing distribution. It is found that excellent sealing results from this method in which the material is consolidated in situ since it is caused to conform with the shape of the opening 14A, 14B. However, severe low temperature cycling can open up channels between the top cap 15 and the KD barrier 13A, 13B which are of a size as to permit non-Knudsen diffusion. This consequence may be avoided by pre-coating the opening 14A, 14B with a sealant, for example a pressure sensitive adhesive, or with a hot melt adhesive. When using the latter material, the top cap 15 together with the barrier 13A, 13B is subsequently raised to the adhesive melting point to effect a stable seal.

The examples shown in the remaining Figures are all intended for use with KD barriers formed of PTFE tape which may or may not be stretched, according to the properties of the tape as initially manufactured. In FIG. 4 the top cap is again shown as 15 and the central opening as 14. Immediately above the top cap 15 is a thin layer 18 of adhesive sealant. This is followed by a piece of PTFE tape 19 constituting the KD barrier and above that an adhesive sealing barrier film 20, the assembly being enclosed by a sealing cap 21 which may, for example, be of nickel foil and which is attached firmly to the top cap 15, for example by spot welding around its perimeter. The sealing film 20 may take the form of a non-porous adhesive coated plastic tape or may be a thin layer on the underside of the cap 21. The sealing cap 21 contains a number of gas access holes drilled annularly at a diameter just greater than that of the KD barrier 19 to allow gas access to the perimeter of the barrier. Diffusion then occurs radially inwardly so that for the purposes of determining the aspect ratio of the barrier, the mean linear dimension along the overall direction of diffusion is equal to the radial dimension of the barrier 19 while the minimum linear dimension across the part of the barrier through which diffusion occurs is the thickness of the barrier.

Figure 4:
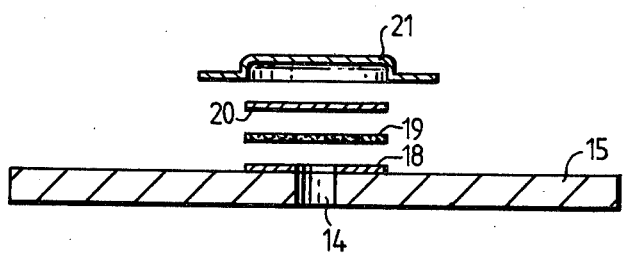
FIGS. 4 and 5 are exploded cross sectional views of further forms of top cap.
Figure 5:
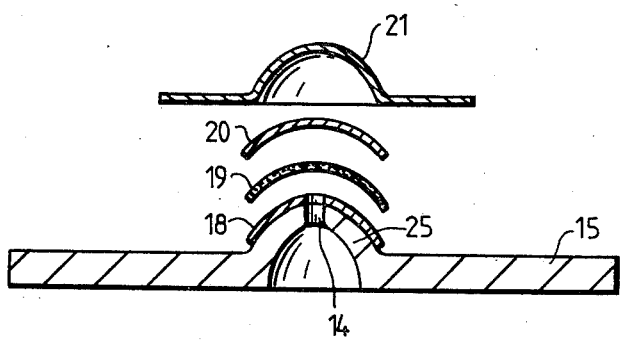

The construction of FIG. 5 includes the same components as that of FIG. 4 and these are therefore identified by the same reference numerals. The construction is modified by the provision of a domed portion 25 surrounding the opening 14 in the centre of the top plate 15. As a consequence, the components 18, 19, 20 and 21 are all similarly domed to fit the portion 25 and it is found that this facilitates sealing.

Figure 6:
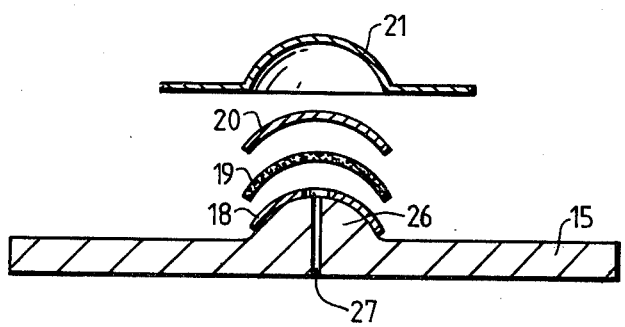
FIG. 6 is an exploded cross sectional view of a top cap similar to that shown in FIG. 5, but including a gas phase barrier in series with the KD barrier.

The construction of FIG. 6 represents a further modification in that the central portion of the top cap 15 is thickened as shown at 26 instead of merely being domed. The components 18, 19, 20 and 21 are all the same as in FIG. 5, but the central opening shown as 27 is appreciably longer, owing to the thickening 26 and is of capillary size so as to define a GP barrier in series with the KD barrier constituted by the PTFE tape 19. The advantage of such a construction is that the small negative co-efficient of the KD barrier is counter-acted by the correspondingly small but positive co-efficient of the GP barrier. By suitable selection of the characteristics of the two barriers, a temperature co-efficient of substantially zero may be obtained which is advantageous in many applications. Other operating characteristics of a sensor using a combination of barriers of the two types are found to be intermediate between the characteristics of KD and GP barrier sensors.

The use of a KD barrier, in particular when it is in the form of consolidated PTFE powder, as illustrated in FIGS. 2 and 3, enables the overall construction to be simplified in a manner not illustrated in the drawings. Since such a KD barrier is hydrophobic and resistant to electrolyte penetration, the waterproofing layer 10 illustrated in FIG. 1 and also the disc 11 may be omitted and the electrode 9 may be mounted directly against the KD barrier. It has also been found that if the electrode material, that is to say catalyst plus PTFE, is pressed directly onto the underside of the top cap 15, the top cap having been first thinly coated with adhesive if necessary, there is a sufficient electrical connection between the electrode and the top cap to avoid the need for the contact strip 7.

The level of the signal required from the sensor depends to some extent on the particular application and also on the active life required in relation to the available anode capacity. It will be seen that considerable variations in signal level may be achieved simply by altering the geometry of the KD barrier, e.g. the signal will be higher the higher the effective diffusion cross sectional area and the shorter the effective diffusion path length.

Examples will now be given of the details of the KD barrier used in various of the constructions described above.

EXAMPLE I

For use in the construction of FIG. 1, a KD barrier was made by stretching a 0.24 mm PTFE tape supplied by W. L. Gore and Associates (UK) Limited, described as clear, unsintered, unstretched tape and having a porosity of about 15%. The tape was stretched laterally to six times its original width and a piece of the stretched tape was used for the barrier, having the following dimensions, cross section 1.5 mm×0.32 mm, length (in the stretched direction) 3 mm. This gave an oxygen sensor having a signal (in ambient air) of 47 mV when loaded with a resistor of 47 ohms (1 mA).

EXAMPLE II

For use with the constructions of either FIGS. 2 or 3, PTFE powder made from GP 1 dispersion manufactured by Imperial Chemical Industries Limited was pressed into an opening 14 of diameter 1.5 mm and length 1.3 mm in a top cap 15. It was then consolidated at a pressure of about 2000 psi and the resultant oxygen sensor gave a signal in ambient air of 40 mV when loaded with a resistance of 47 ohms (0.85 mA).

EXAMPLE III

This was a modification of Example II in that the opening 14 was slightly tapered and had a minimum diameter of 0.5 mm and a length of 2.5 mm. It was filled with the same PTFE powder as in Example II and this was consolidated at 5000 p.s.i. The resultant oxygen sensor gave a signal in ambient air of 9.0 mV when loaded with a 47 ohms resistor.

EXAMPLE IV

For use with a top cap as illustrated in FIG. 5, a piece of "Tygaflor" R 12.8 gauge 7T PTFE tape was used, as received, in the form of a disc of 6 mm diameter in conjunction with a top cap 15 having an opening 14 of 1.3 mm diameter and the resultant oxygen sensor gave a signal of 45 mV in ambient air when loaded with 47 ohms.

The KD sensors quoted in these Examples and other sensors made in a similar fashion all had the characteristics, which as described earlier, distinguish them uniquely from SM or GP barrier sensors. For example, (1) Temperature co-efficient. Low negative co-efficient close to −0.17% per °C. (cf SM sensors, high positive of the order of 2% to 3% per °C. GP barrier sensors, positive around +0.17% per °C.).

(2) Pressure co-efficient. At a given percentage oxygen the signal from the KD sensors is substantially proportional to the total pressure indicating that they are responding directly to partial pressure. (GP barrier sensors give a steady state signal substantially independent of total pressure, indicating that they are responding to % oxygen rather than partial pressure).

It will be readily appreciated that these differing characteristics can lead to specific advantages for specific applications. If a substantially zero temperature co-efficient is required, the construction of FIG. 6 may be used in accordance with the following Example.

EXAMPLE V

For this purpose a KD barrier was composed of two thicknesses of the same PTFE tape as in Example IV and has a diameter of 6 mm. When used as the sole barrier, this gave a signal from the resultant sensor of about 2 mA in ambient air. This was used in series with a capillary shown as 27 in FIG. 6 having the following dimensions, length 2.5 mm and diameter 0.29 mm. A sensor using this capillary alone as a GP barrier also gave a signal of 2 mA in ambient air. When the two barriers were used in series, the resultant sensor gave a signal of 46 mV when loaded with a 47 ohms resistor. The temperature co-efficient measured between 0° C. and 40° C. was close to zero (less than +0.01% of signal per °C.) and the pressure co-efficient in ambient air was half that of a corresponding sensor using only a KD barrier. This confirmed that the characteristics of a sensor using a KD barrier in series with a GP barrier were intermediate between the characteristics of sensors using a KD barrier and a GP barrier respectively.

We claim:

1. An electro-chemical sensor for measuring concentrations of electro-chemically reactable gas or vapour in accordance with a limiting current principle, comprising:
   a casing;
   a sensing electrode;
   a counter electrode;
   a means for restricting gas or vapour access to said sensing electrode, said means comprising a porous diffusion barrier having a temperature co-efficient which is negative with respect to diffusion rate wherein substantially all active pores in said barrier are sufficiently small so that diffusion through them is in accordance with the Knudsen principle and diffusion occurs by a diffusion mechanism effectively determined solely by collisions between diffusing molecules and walls of pores in said barrier, said barrier proportioned such that the barrier's minimum linear dimension measured at right angles to the overall direction of diffusion is less than twice the mean linear dimension along the direction of diffusion.

2. A sensor according to claim 1 and including a gas phase diffusion barrier in series with said porous diffusion barrier.

3. A sensor according to claim 2 in which said gas phase diffusion barrier is constituted by a capillary.

4. A sensor according to claim 2 or claim 3 in which the characteristics of said porous diffusion barrier and said gas phase diffusion barrier are so matched as to give substantially zero temperature co-efficient.

5. An electro-chemical sensor as claimed in claim 1, wherein said electro-chemically reactable gas or vapour is oxygen.

6. A sensor according to any of claims 1 or 5 in which said barrier comprises a piece of unsintered PTFE tape, means sealing said tape across an opening in said cell casing and an impervious cover covering said tape, said cover being formed with gas access openings at points beyond the outer limits of said tape whereby diffusion occurs radially inwardly through said tape from said gas access openings in said cover to said opening in the casing.

7. A sensor according to any of claims 1 or 5 in which said barrier comprises a piece of unsintered PTFE tape and means sealing said tape within an opening in said casing.

8. A sensor according to claim 7 in which said tape has been stretched across its width subsequent to manufacture and is arranged in the opening in such a way that diffusion through the barrier is along the direction of stretching.

9. A sensor according to any of claims 1 or 5 in which said barrier comprises a body formed of compressed PTFE powder, said body being sealed within an opening in said casing by consolidation in situ.

* * * * *